US00PP18940P2

(12) United States Plant Patent
Smith

(10) Patent No.: US PP18,940 P2
(45) Date of Patent: Jun. 17, 2008

(54) ***CHRYSANTHEMUM* PLANT NAMED 'JOLLY YOCHERYL'**

(50) Latin Name: *Chrysanthemum×morifolium*
Varietal Denomination: Jolly Yocheryl

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/641,535

(22) Filed: Dec. 18, 2006

(51) Int. Cl.
*A01H 5/00* (2006.01)

(52) U.S. Cl. ..... Plt./293

(58) Field of Classification Search ..... Plt./293
See application file for complete search history.

(56) References Cited

U.S. PATENT DOCUMENTS

PP8,982 P * 11/1994 VandenBerg ..... Plt./293

* cited by examiner

*Primary Examiner*—Wendy C. Haas
(74) *Attorney, Agent, or Firm*—C. A. Whealy

(57) ABSTRACT

A new and distinct cultivar of *Chrysanthemum* plant named 'Jolly Yocheryl', characterized by its compact, upright and outwardly spreading plant habit; freely branching habit; dense and full plant habit; uniform and freely flowering habit; decorative-type inflorescences with elongated oblong to obovate-shaped ray florets; red-colored ray florets; and natural flowering about October 8$^{th}$ in the Northern Hemisphere.

1 Drawing Sheet

Botanical designation: *Chrysanthemum×morifolium.*
Cultivar denomination: 'Jolly Yocheryl'.

BACKGROUND OF THE INVENTION

The present invention relates to a new and distinct cultivar of *Chrysanthemum* plant, botanically known as *Chrysanthemum×morifolium,* commercially grown as a garden *Chrysanthemum* and hereinafter referred to by the name 'Jolly Yocheryl'.

The objective of the breeding program is to create new garden-type *Chrysanthemum* cultivars having inflorescences with desirable inflorescence forms, attractive floret colors and good garden performance.

The new *Chrysanthemum* is a naturally-occurring whole plant mutation of unnamed proprietary selection of *Chrysanthemum×morifolium,* not patented. The new *Chrysanthemum* was discovered and selected by the Inventor as a single flowering plant within a population of plants of the parent selection in December, 2003, in Alva, Fla. The selection of this plant was based on its desirable inflorescence color and good form and substance.

Asexual reproduction of the new *Chrysanthemum* by vegetative cuttings was first conducted in Alva, Fla. in February, 2004. Asexual reproduction by cuttings has shown that the unique features of this new *Chrysanthemum* are stable and reproduced true to type in successive generations.

SUMMARY OF THE INVENTION

Plants of the cultivar Jolly Yocheryl have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Jolly Yocheryl'. These characteristics in combination distinguish 'Jolly Yocheryl' as a new and distinct garden *Chrysanthemum* cultivar:

1. Compact, upright and outwardly spreading plant habit.
2. Freely branching habit; dense and full plant habit.
3. Uniform and freely flowering habit.
4. Decorative-type inflorescences with elongated oblong to obovate-shaped ray florets.
5. Red-colored ray florets.
6. Natural season flowering about October 8$^{th}$ in the Northern Hemisphere.

In side-by-side comparisons conducted in Alva, Fla., plants of the new *Chrysanthemum* differed from plants of the parent selection in the following characteristics:

1. Plants of the new *Chrysanthemum* flowered later than plants of the present selection when grown under natural season conditions.
2. Ray florets of plants of the new *Chrysanthemum* were more red in color than ray florets of plants of the parent selection.

Plants of the new *Chrysanthemum* can be compared to plants of the *Chrysanthemum* cultivar Raquel, disclosed in U.S. Plant Pat. No. 8,982. In side-by-side comparisons conducted in Alva, Fla., plants of the new *Chrysanthemum* differed from plants of the cultivar Raquel in the following characteristics:

1. Plants of the new *Chrysanthemum* were more uniformly mounded than plants of the cultivar Raquel.
2. Plants of the new *Chrysanthemum* had larger inflorescences than plants of the cultivar Raquel.
3. Ray florets of plants of the new *Chrysanthemum* were lighter red in color than ray florets of plants of the cultivar Raquel.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph at the bottom of the sheet comprises a side perspective view of a typical flowering plant of 'Jolly Yocheryl'.

The photograph at the top of the sheet is a close-up view of typical inflorescences of 'Jolly Yocheryl'.

DETAILED BOTANICAL DESCRIPTION

The aforementioned photographs and following observations and measurements describe plants grown in Fletcher, N.C. during the summer in an outdoor nursery and under conditions and practices which approximate those generally used in commercial garden *Chrysanthemum* production. During the production of the plants, day temperatures averaged 29° C. and night temperatures averaged 16° C. Plants were grown in 15-containers, exposed to long day/short night conditions and pinched about two weeks later. About two weeks after the pinch, the photoinductive short day/long night treatments were started. Plants used in the photographs and for the description were about three months old. In the following description, color references are made to The Royal Horticultural Society Colour Chart, 1995 Edition, except where general terms of ordinary dictionary significance are used.

Botanical classification: *Chrysanthemum×morifolium* cultivar Jolly Yocheryl.

Parentage: Naturally-occurring whole plant mutation of an unnamed proprietary selection of *Chrysanthemum× morifolium,* not patented.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Herbaceous decorative-type garden *Chrysanthemum.* Stems upright and outwardly spreading giving a uniformly mounded appearance to the plant. Freely branching habit, about six lateral branches develop after removal of terminal apex (pinching) each with numerous secondary laterals; dense and full plant habit. Strong and vigorous growth habit.

*Plant height.*—About 21 cm.

*Plant width.*—About 27 cm.

*Lateral branches.*—Length: About 20 cm. Diameter: About 6 mm. Internode length: About 1.5 cm. Strength: Strong. Texture: Pubescent. Color: 148B.

*Leaves.*—Arrangement: Alternate, simple. Length: About 5.2 cm. Width: About 4.3 cm. Apex: Broadly acute. Base: Attenuate. Margin: Palmately lobed, sinuses between lateral lobes mostly parallel. Texture, upper and lower surfaces: Fine pubescence; veins prominent on lower surface. Color: Developing foliage, upper and lower surfaces: 147A. Fully expanded foliage, upper surface: 147A; venation, 147B. Fully expanded foliage, lower surface: 147B; venation, 147B. Petiole: Length: About 8 mm. Diameter: About 2.5 mm. Texture, upper and lower surfaces: Pubescent. Color, upper and lower surfaces: 147B.

Inflorescence description:

*Appearance.*—Decorative-type inflorescence form with elongated oblong to obovate-shaped ray florets. Inflorescences borne on terminals above foliage. Disk and ray florets arranged acropetally on a capitulum. Inflorescences not fragrant.

*Flowering response.*—Under natural season conditions, plants flower about October 8$^{th}$ in the Northern Hemisphere. At other times of the year, inflorescence initiation and development can be induced under short day/long night conditions (at least 13.5 hours of darkness). Early flowering habit; plants exposed to photoinductive short day/long night conditions flower about 55 days later.

*Postproduction longevity.*—Inflorescences maintain good color and substance for about three weeks in an outdoor nursery.

*Quantity of inflorescences.*—About 21 inflorescences develop per lateral branch.

*Inflorescence bud.*—Height: About 1.2 cm. Diameter: About 1 cm. Shape: Ovoid. Color: 182A.

*Inflorescence size.*—Diameter: About 4.5 cm. Depth (height): About 2 cm. Disc diameter: About 3 mm; inconspicuous. Receptacle diameter: About 1.5 cm. Receptacle height: About 4 mm.

*Ray florets.*—Shape: Elongated-oblong to obovate. Orientation: Initially upright, then about 45° to 60° from vertical; eventually perpendicular to peduncle. Aspect: Initially incurved, then mostly concave. Length: About 2.2 cm. Width: About 8 mm. Apex: Nearly round to slightly emarginate. Base: Acute. Margin: Entire. Texture, upper and lower surfaces: Smooth, glabrous, satiny. Number of ray florets per inflorescence: About 170 arranged in about 15 to 16 whorls. Color: When opening, upper surface: 173A to 173B. When opening, lower surface: 179D. Fully opened, upper surface: 179B; color becoming closer to 173D with development. Fully opened, lower surface: 158B to 158C; color becoming closer to 158A with development.

*Disc florets.*—Shape: Tubular, elongated. Length: About 2.5 mm. Diameter: About 1 mm. Number of disc florets per inflorescence: About 35. Color, immature: Apex: Close to 15C. Mid-section: Close to 15D. Base: Close to 145D. Color, mature: Apex: close to 15B. Mid-section: Close to 15C. Base: Close to 145D.

*Phyllaries.*—Number of phyllaries per inflorescence: About 26 arranged in about two whorls. Length: About 6 mm. Width: About 2.5 mm. Shape: Ligulate. Apex: Acute. Base: Truncate. Texture, upper surface: Smooth, waxy. Texture, lower surface: Pubescent. Color, upper surface: Close to 137B. Color, lower surface: Close to 137A.

*Peduncles.*—Length: About 4.2 cm. Diameter: About 2 mm. Angle: About 45° from vertical. Strength: Strong. Texture: Pubescent; longitudinally ridged. Color: Close to 148A.

*Reproductive organs.*—Androecium: Stamen number: About five per floret. Filament length: Less than 1 mm. Filament color: Close to 145D. Anther length: Less than 1 mm. Anther shape: Oblong. Anther color: Close to 15B. Pollen amount: None observed.

Gynoecium: Pistil length: About 5 mm. Stigma shape: Bi-parted. Stigma color: Close to 4B. Style length: About 2 mm. Style color: Close to 4D. Ovary color: Close to 155A.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and to tolerate temperatures from about 0° C. to about 38° C.

It is claimed:

1. A new and distinct *Chrysanthemum* plant named 'Jolly Yocheryl' as illustrated and described.

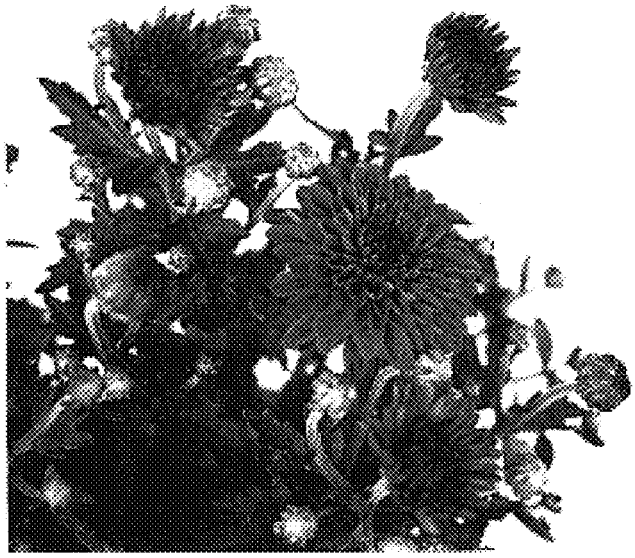
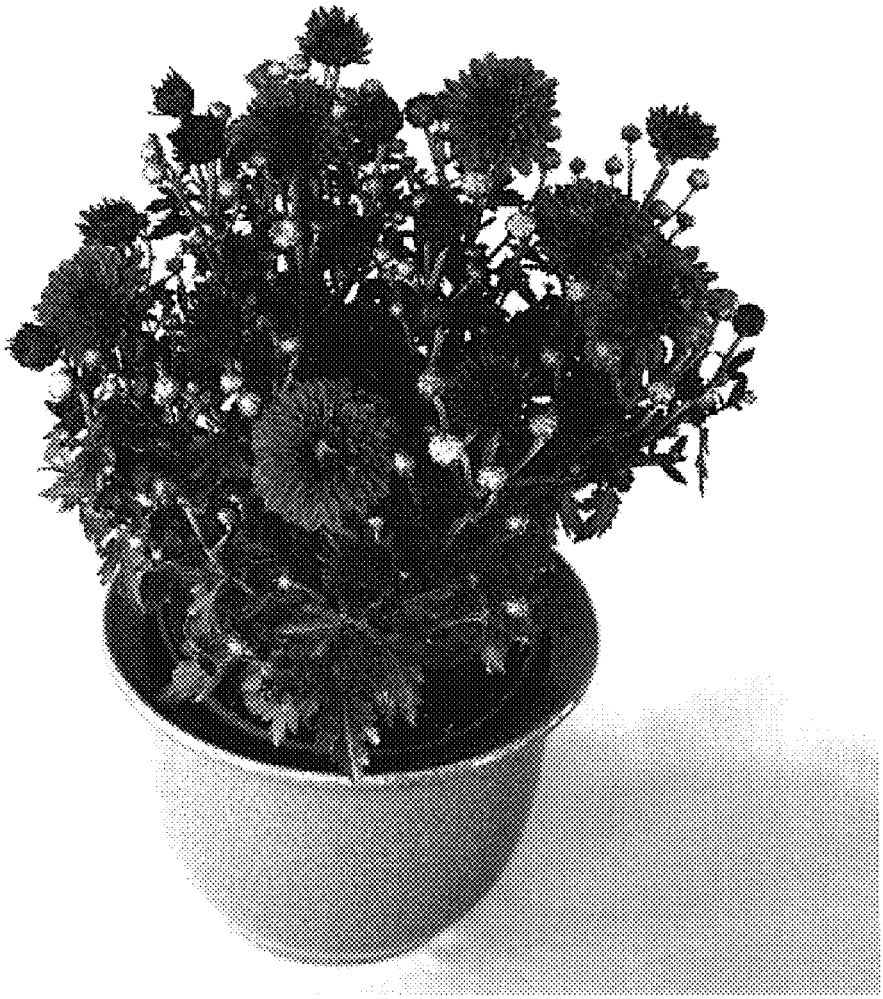

* * * * *